(12) United States Patent
Faanes et al.

(10) Patent No.: US 11,175,272 B2
(45) Date of Patent: Nov. 16, 2021

(54) SUBSEA GAS QUALITY ANALYSIS (71) Applicant: Equinor Energy AS, Stavanger (NO)

(72) Inventors: Audun Faanes, Trondheim (NO); Pablo Matias Dupuy, Hommelvik (NO); Torbjørn Vegard Løkken, Ranheim (NO); Anita Berså Hansen, Trondheim (NO); Karl Herman Frantzen, Nesltun (NO)

(73) Assignee: Equinor Energy AS, Stavanger (NO)

( * ) Notice: Subject to any disclaimer, the term of this patent is extended or adjusted under 35 U.S.C. 154(b) by 200 days.

(21) Appl. No.: 16/344,970

(22) PCT Filed: Oct. 26, 2017

(86) PCT No.: PCT/NO2017/050274
§ 371 (c)(1),
(2) Date: Apr. 25, 2019

(87) PCT Pub. No.: WO2018/080318
PCT Pub. Date: May 3, 2018

(65) Prior Publication Data
US 2019/0271678 A1   Sep. 5, 2019

(30) Foreign Application Priority Data
Oct. 26, 2016   (GB) ..................... 1618116

(51) Int. Cl.
*G01N 33/00* (2006.01)
*G01N 33/22* (2006.01)
(Continued)

(52) U.S. Cl.
CPC ....... *G01N 33/225* (2013.01); *E21B 41/0007* (2013.01); *E21B 41/06* (2013.01);
(Continued)

(58) Field of Classification Search
CPC ............. G01N 33/225; G01N 30/7206; G01N 33/0016; G01N 30/88; G01N 2030/025;
(Continued)

(56) References Cited

U.S. PATENT DOCUMENTS

2007/0125233 A1   6/2007   Bostrom et al.

FOREIGN PATENT DOCUMENTS

| GB | 2303716 A | 2/1997 |
| WO | 2004027677 A1 | 4/2004 |

(Continued)

OTHER PUBLICATIONS

Dec. 14, 2017—(WO) International Search Report and Written Opinion—APP PCT/NO2017/050274.
May 30, 2017—(GB) Search Report—APP 1618116.6.

*Primary Examiner* — Robert R Raevis
(74) *Attorney, Agent, or Firm* — Banner & Witcoff, Ltd.

(57) ABSTRACT

Apparatus for monitoring the quality of gas in a process stream at a subsea location comprises: a container for permanent installation at the location; one or more devices for analysing gas quality, said devices being located in the container; and means for supplying a sample of gas from the process stream to the said one or more devices; wherein the pressure within the container is maintained at or near to atmospheric pressure. The invention also extends to a method of monitoring the quality of gas in a process stream at a subsea location.

19 Claims, 5 Drawing Sheets

(51) Int. Cl.
*G01N 30/72* (2006.01)
*G01N 30/88* (2006.01)
*E21B 49/00* (2006.01)
*E21B 41/00* (2006.01)
*E21B 43/01* (2006.01)
*E21B 41/06* (2006.01)
*G01N 30/02* (2006.01)
*G01N 30/86* (2006.01)
*E21B 49/08* (2006.01)

(52) U.S. Cl.
CPC ............ *E21B 43/01* (2013.01); *E21B 49/001* (2013.01); *G01N 30/7206* (2013.01); *G01N 30/88* (2013.01); *G01N 33/0016* (2013.01); *E21B 49/0875* (2020.05); *G01N 30/8665* (2013.01); *G01N 2030/025* (2013.01); *G01N 2030/8854* (2013.01)

(58) Field of Classification Search
CPC ....... G01N 30/8665; G01N 2030/8854; G01N 33/0004; G01N 33/0006; G01N 33/0022; G01N 2001/1031; G01N 2001/1037; G01N 2001/105; E21B 49/001; E21B 41/0007; E21B 43/01; E21B 41/06; E21B 49/0875
USPC ...... 73/23.22–23.27, 23.42, 1.02, 1.06, 1.07, 73/863.81, 864.81; 166/250.01, 250.06, 166/264, 335–368
See application file for complete search history.

(56) References Cited

FOREIGN PATENT DOCUMENTS

| | | |
|---|---|---|
| WO | 2008067296 A2 | 6/2008 |
| WO | 2013130924 A1 | 9/2013 |

SUBSEA GAS QUALITY ANALYSIS

The present application is a U.S. National Phase of International Application No. PCT/NO2017/050274, filed on Oct. 26, 2017, designating the United States of America, and claims priority to British Patent Application No. 1618116.6, filed Oct. 26, 2016. This application claims priority to and the benefit of the above-identified applications, each of which is fully incorporated by reference herein.

The invention is concerned with a method and apparatus for analyzing the quality of gas at a subsea location.

During the extraction of natural gas, it is important to determine quality parameters (that is, parameters which affect the quality of the gas), such as gas composition, calorific value, $H_2S$ content, $CO_2$ content, moisture content, mercury content, glycol content, hydrocarbon dew point, $O_2$ content, methanol content, and so on.

Monitoring of a process stream in order to determine its properties is normally carried out on production or processing platforms. A sample of the gas in the process stream is removed and analyzed with measurement technology, such as gas chromatography.

The process stream is usually at a relatively high pressure (considerably above atmospheric pressure). However, measurement technology such as gas chromatography requires the gas sample to be depressurized to a pressure at or close to atmospheric pressure, and also normally requires the sample to be vented to atmosphere after analysis.

There is increasing interest in subsea gas processing (that is, where the gas from the well is processed near the well at the seabed, rather than being brought to the surface for processing at topside infrastructure such as a production or processing platform). Existing technologies for monitoring of gas quality parameters are not normally suitable for subsea installations, for a variety of reasons. In particular, most gas monitoring devices are designed to operate at atmospheric pressure, and require frequent maintenance. Further, an analyzed gas stream subsea cannot easily be vented to atmosphere.

A device is known from WO 2008/067296 which is capable of analyzing a fluid sample using gas chromatography in hostile environments (such as down-hole). In a down-hole environment, the pressure can reach 20,000 psi (around 140 MPa, or around 1360 atmospheres), and the temperature can reach 200° C., and so the device must be capable of withstanding such conditions.

Carrier gas for the gas chromatographs in the device of WO 2008/067296 is stored within the device, and waste gas from the gas chromatography process is also stored within the device (as it cannot be vented to the environment). Since the device must be fairly small (to allow it to be used in a down-hole environment), the amount of carrier gas and waste gas which can be stored is limited, and so the device cannot be used for prolonged periods of time.

The invention has been made in view of the above circumstances, and it is an object of at least the preferred embodiments of the invention to provide a method and apparatus which can be used for gas quality monitoring at subsea installations.

According to a first aspect of the present invention, there is provided apparatus for monitoring the quality of gas in a process stream at a subsea location; comprising: a container for permanent installation at the subsea location; one or more devices for analysing gas quality, said devices being located in the container; and means for supplying a sample of gas from the process stream to the said one or more devices; wherein the pressure within the container is maintained at or near to atmospheric pressure.

The apparatus is intended to remain in place at the subsea location for a considerable period (at least several months, and possibly several years), and to carry out monitoring of the process stream throughout this period.

Since the pressure inside the container is at or near to atmospheric pressure, standard gas monitoring devices can be used with no (or minimal) adaptation.

The sample taken from the process stream will be at a high pressure. It may be possible to use gas monitoring devices which are capable of accepting a high pressure stream; alternatively, the apparatus may further comprise means for reducing the pressure of the sample of gas from the pressure of the process stream to the pressure within the container. This reduces the need to modify the monitoring devices.

Any suitable form of gas monitoring device may be used. However, it is preferred for at least one of the devices for analysing gas quality is a gas chromatograph.

A gas chromatograph requires carrier gas to operate, and may also require calibration gas in order to produce reliable results. Thus, in a preferred form, the apparatus further comprises means for supplying carrier gas and/or calibration gas to the gas chromatograph.

In one preferred form, the means for supplying carrier gas and/or calibration gas comprises a reservoir holding said carrier gas and/or calibration gas, said reservoir preferably being in the form of one or more gas bottles. In an alternative preferred form, the means for supplying carrier gas and/or calibration gas comprises an umbilical.

After the gas has been analysed, it is necessary to remove it from the container; if this is not done, then pressure will build up inside the container, possibly to the point where the operation of the gas monitoring devices will be affected. Thus, in a preferred form, the apparatus further comprises means for discharging gas from the container after analysis. For example, the gas may be compressed (to increase its pressure) and discharged to the undersea environment, or returned to the main gas flowline.

In a particularly preferred form, the means for discharging gas includes a reservoir for the analyzed gas. The reservoir can also accommodate any other gas produced during the analysis (such as waste carrier gas).

Means may be provided for removing gas from the reservoir. These means may take the form of an umbilical. A single umbilical may be used for the removal of gas from the apparatus, the supply of carrier gas and/or calibration gas, and for communication with a topside or onshore installation.

Means may also be provided for controlling the temperature within the container, and this may involve heating or cooling the container, or heat tracing of the equipment containing the gas such as piping and valves. This may be necessary to avoid condensation of constituents of the process stream and/or the calibration gas, or to ensure that the measurements of gas quality by the analysis devices are reliable.

According to a second aspect of the present invention, there is provided a method of monitoring the quality of gas in a process stream at a subsea location, including the steps of: providing a container at said subsea location, said container including a volume at or near atmospheric pressure accommodating one or more devices for analysing gas quality; taking a sample of gas from the process stream; reducing the pressure of the sample of gas to or to near to atmospheric pressure; and supplying said sample of gas to said one or more devices for analysis.

The method may further comprise the step of discharging gas after analysis.

Preferably, the sample taken from the process stream is in a single phase, as this simplifies the analysis procedure.

In an alternative form, the sample taken from the process stream includes a gas phase and a liquid phase, which are analysed separately.

Preferably, the method further comprises the step of controlling the temperature within the container, either overall or within specific parts of the container.

Preferred embodiments of the invention will now be described by way of example only and with reference to the accompanying Figures, in which.

Figure 1:
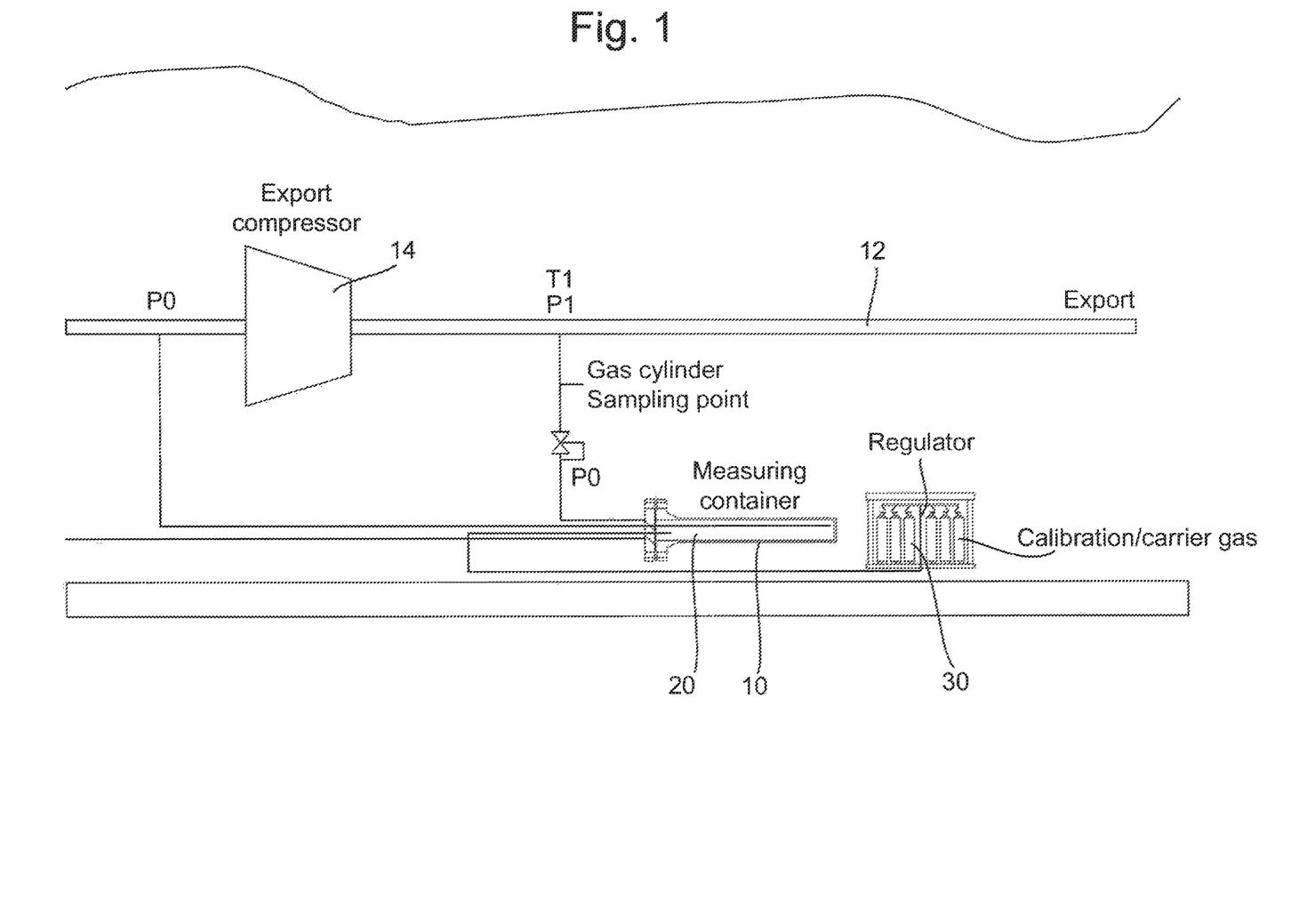
FIG. 1 is a schematic view of an analysis device installed next to a process stream.

FIG. 1 shows, in a highly schematic form, an analysis device 10 installed near to a subsea process stream 12. The analysis device comprises a container 20, whose internal pressure can be maintained at or near to atmospheric pressure. The container accommodates one or more analysis devices (such as gas chromatographs) which need to be at (or near to) atmospheric pressure in order to function. The container and the analysis devices will be described in more detail later.

The container 20 in FIG. 1 is located so that gas is taken from the process stream 12 downstream of a compressor 14. Some of the gas taken from the process stream 12 is led into the container 20 for analysis, and the remainder of the gas taken from the process stream is returned to the process stream upstream of the compressor 14. However, the gas may be taken from and returned to the stream at other points, as will be described later.

The container is also shown in association with a number of gas bottles 30. As is well known, gas chromatographs require a supply of carrier gas to operate, and this carrier gas may be supplied in bottles. Further, it may also be necessary for the gas chromatograph to be recalibrated (or checked against a calibration gas for quality control), and this will require a supply of calibration gas. This may also be supplied in bottles. Of course, other means (such as an umbilical) may be provided for supplying the necessary carrier gas and/or calibration gas, and this will be described in more detail later.

The container 20 is in communication with an installation above sea level (for example, a production platform or an onshore installation, not shown), so that the results of the gas quality analysis can be communicated to the installation, and gas production can be controlled accordingly. This communication line may also be used to supply power to the container 20 and the analysis devices accommodated therein. The system may be supervised from the installation, and control actions such as initiating a recalibration may be done from there, The container 20 (and ancillary equipment such as the gas bottles 30) can be retrieved from its undersea location and brought to the surface as necessary, for example for maintenance, recalibration of the analysers (if this cannot be carried out subsea), and replenishment of gas supplies. However, this retrieval will take place relatively infrequently (no more often than every six months, and more probably every one or two years), and so the container can be considered to be permanently installed at its undersea location. The container may be retrieved as a single unit, or may be divided into a number of separately retrievable modules, so that (for example) the module containing the reservoirs of the carrier gas and the calibration gas may be retrieved separately.

Figure 2:
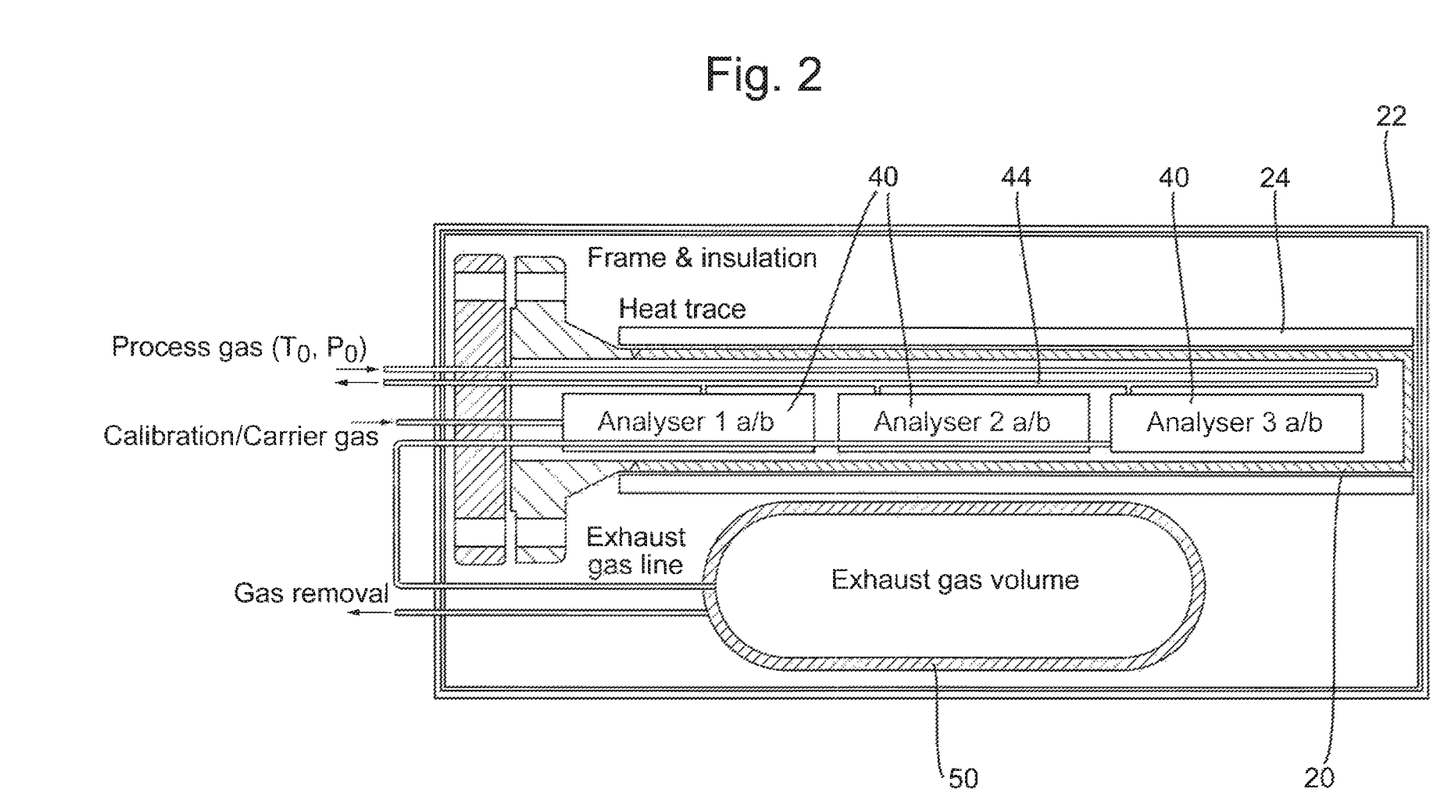
FIG. 2 is a view of a first version of the analysis device.

FIG. 2 shows a first version of the analysis device in more detail.

Figure 3:
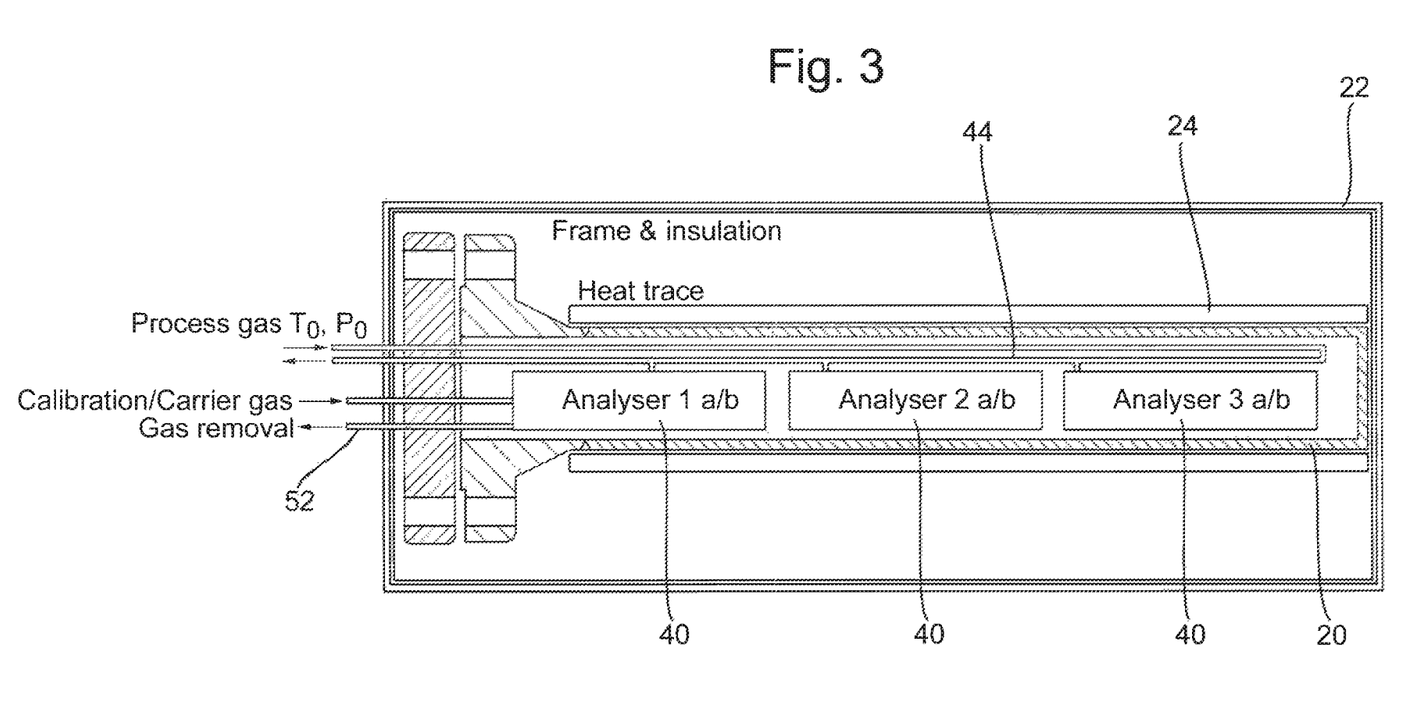
FIG. 3 is a view of a second version of the analysis device.

The device consists generally of a rigid hollow container 20, capable of resisting the forces exerted by the external pressure of the sea water. FIGS. 1, 2 and 3 all show the container 20 as a flanged vessel with a circular cross-section, but other cross-sections may be used as appropriate. A container with a square or rectangular cross-section may be easier to install and replace, whereas a slim and long design would reduce wall thickness and therefore weight. The container is fitted in a frame 22 for handling and structural requirements.

The container holds one or more (in the Figure, three) analysers 40 which can determine various aspects of gas quality, one of which may be a gas chromatograph. The pressure inside the container 20 is maintained at (or near to) atmospheric pressure, so that analysers designed for operation at or near sea level can be used with only minor modifications (and, ideally, no modifications).

Gas taken from a process stream 12 (see FIG. 1) can be introduced into the container 20 via a line 44, and this line is in communication with each of the analysers, so that gas can be led from the line to each analyser. Further, gas leaving each of the analysers can be led to a dedicated reservoir 50 for exhaust gas, which can be emptied when required. It may also be possible to return the gas to the process stream, although this may require pressurization of the analyzed gas.

The container 20 is surrounded by a heating device 24, such as a heat trace, to allow the temperature within the container 20 to be maintained at a desired level (for example, to avoid the condensation of components in the gas stream). Of course, any suitable means may be used to heat the container 20.

The heating device 24 may not be required if the equipment inside the container generates sufficient heat. Indeed, it may be necessary to provide cooling equipment if the equipment generates considerable heat.

Further, the entire container, including the heating device, is surrounded by insulation, to avoid excessive loss of heat to the surrounding sea water (which is typically between 0° C. and 10° C.). Thus, the conditions within the container can be maintained at (or near to) those that would be encountered topside, so that the analysers 40 can be used in a subsea location with no (or minimal) adaptation required.

It may also be possible to use the container without temperature control, as long as the temperature can be controlled in the tubing and other equipment that contains the sample gas during analysis. In this case, it would also be necessary to control the temperature of the calibration gas in order to avoid the gas entering a two-phase range.

FIG. 3 shows a similar form of the device, except that instead of having a dedicated reservoir for exhaust gas, gas 52 leaving the analysers 40 is directed out of the container (for example, to be returned to the process stream, or to be vented via an umbilical or similar). As shown, this can reduce the overall size of the installation.

The sampling point for the gas to be analysed should be located between the last step of the gas processing system and the export (for example, after the export compressor 14 shown in FIG. 1). Further, the samples taken at the sampling point should be representative of the export gas, and since this is more challenging where there is both gas and liquid present at the sampling point, it is preferred for the sample to be in a single phase, as would normally be the case downstream of a compressor. However, it is still possible to perform a satisfactory analysis of the sample even if gas and liquid are present.

If the gas is sampled downstream of the export compressor (as shown in FIG. 1), then the process stream 12 may be at a high pressure and temperature (above 150 bar and 100° C.), and so may be in a single phase. Single phase sampling is desirable, as there is a very low risk of presence of liquids under normal operation. Of course, it will be necessary to reduce the pressure of the gas down to (or near to) atmospheric pressure, in order for the gas to be analysed by a gas chromatograph in the container 20, and this will be described later.

Figure 4:
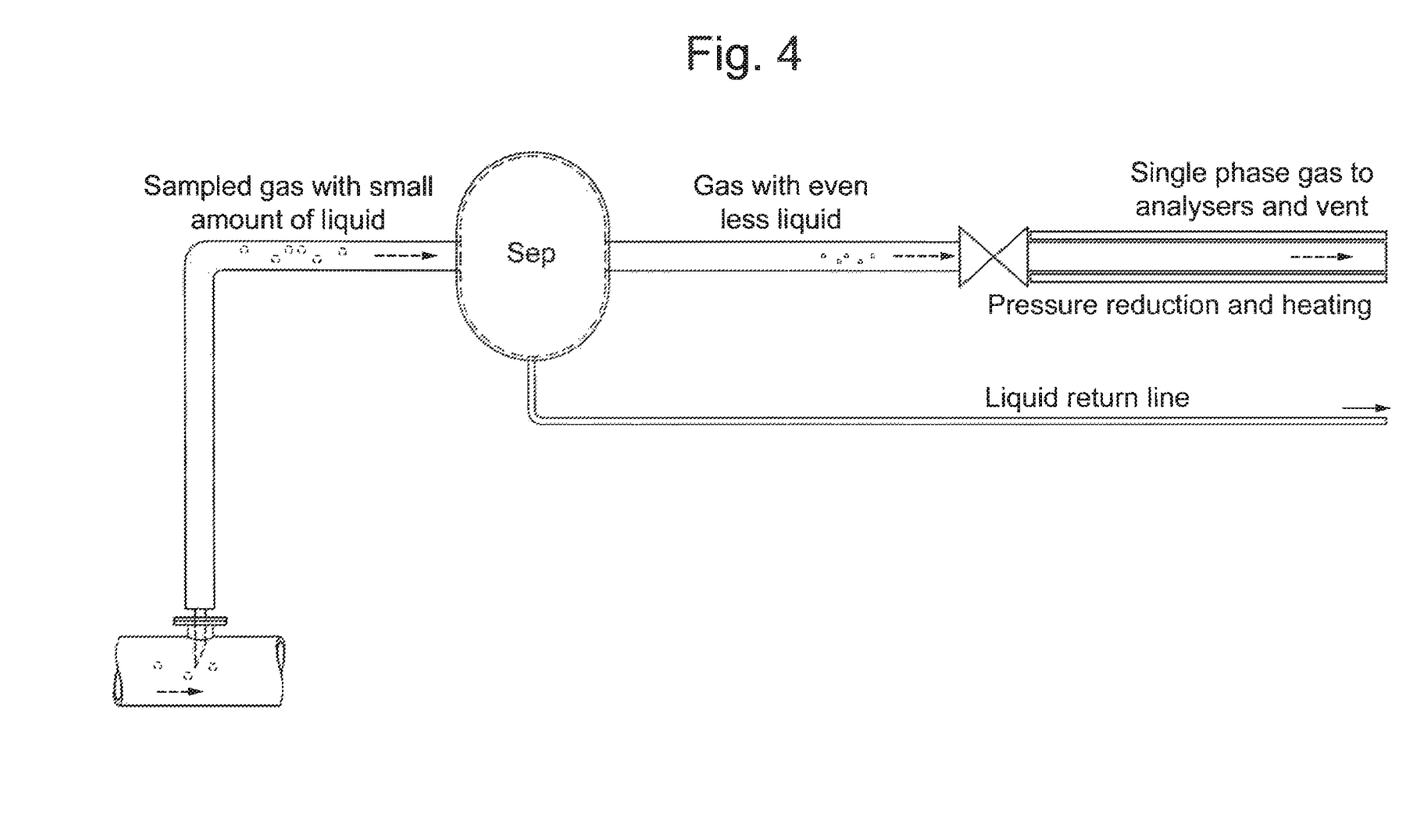
FIG. 4 is a schematic view illustrating the sampling of a two-phase process stream.

In a second design option (shown in a highly schematic manner in FIG. 4), which may be required in some installations, the gas is sampled downstream of a liquid removal unit (scrubber) (in cases where the pressure is kept high throughout the gas processing system). In this case the process stream will be at high pressure and low temperature (above 150 bar and 10° C.). While the main part of the process stream will be gas, there will also be small amounts of liquids present under normal operation (generally below 0.001 vol %), and these liquids will normally be glycol and water. In some cases, hydrocarbon liquids may also be present.

Two phase sampling (that is, sampling where the sample includes gas and liquid) presents a number of problems. In particular, the amount of liquid carry-over and the trace components (and hydrocarbons) dissolved in it could be of relevance to the overall assessment of the quality parameters. To deal with this, the analysers inside the container are used to assess the gas phase, and a separate liquid carry-over measurement is used to assess the components associated with the liquid carry-over. The overall export gas quality can thus be determined based on the separate assessments of the gas phase and the liquid carry-over.

The effects of combining gas and carry-over partial results to provide an overall result will be different for different gas quality parameters. For example, water content is expected to be very sensitive to both partial results. On the other hand, gross calorific value and hydrocarbon composition are only sensitive to the measurements in the gas phase.

It is important that the vapour-liquid equilibrium in the system should not be disturbed. Accordingly, the pressure and the temperature of the sample must be kept constant (at scrubber conditions) until the liquid phase is separated from the vapour phase. When exiting the scrubber the natural gas, water and glycol will be close to equilibrium, but even small changes in pressure and especially temperature can disturb the equilibrium. As long as these conditions are obtained, the gas and liquid can be separated without changing the water content in the natural gas.

Figure 5:
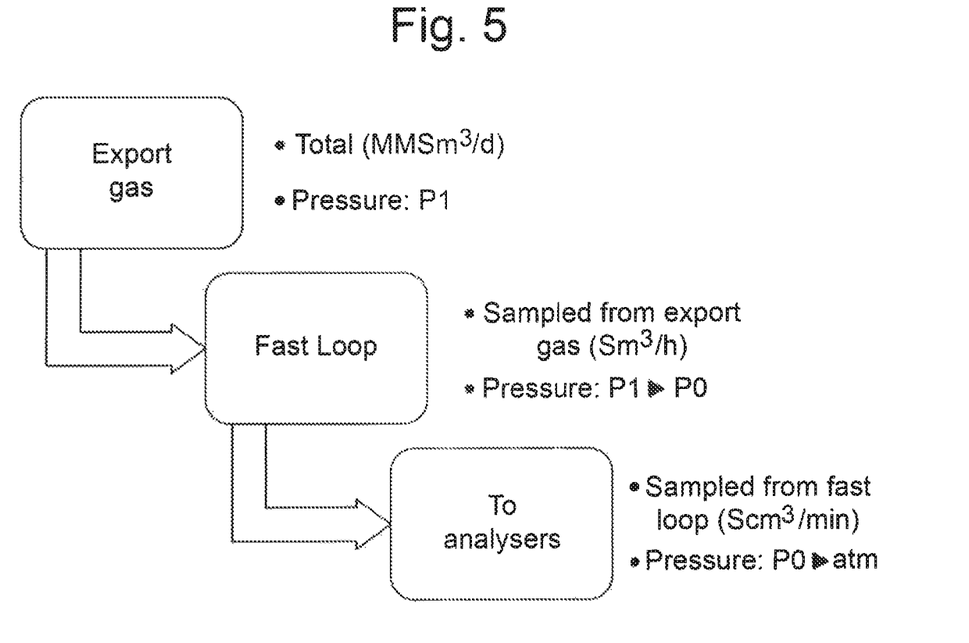
FIG. 5 illustrates the sampling and pressure reduction process.

FIG. 5 shows in a highly schematic manner how the single-phase gas is sampled for analysis. A gas sample is taken from the gas process stream (marked as "Export gas") by a loop with continuous flow. This resembles a fast loop used for topside applications to reduce response time for the system, and is labelled as "Fast loop". A part of the flow through the fast loop is taken out and separately sent to each analyser system.

Returning now to FIG. 1, this shows an example of a fast loop return line tie-in at the suction side of the compressor 14. As mentioned above, each analyser device 40 is arranged inside the container 20 and thus is at or near atmospheric pressure. Accordingly, the container 20 must also include a pressure reduction section, so that the high-pressure gas in the process stream 12 can have its pressure reduced to (or to near to) atmospheric pressure. (Of course, if analysers capable of operating at (or close to) export pressure are used, then this pressure reduction can be avoided; however, this limits considerably the range of analysis devices which can be used). Filters or similar devices may also be required in order to avoid contamination or plugging of the pressure reduction and analyzer systems.

A relatively large sample is taken from the main process stream and circulated in the fast loop to reduce the response time in the system. The fast loop also ensures that fresh and representative samples are reaching the analysers. Most of the gas in the fast loop will be returned to the process stream, to avoid unnecessary ventilation and losses of gas. Since (as shown in FIG. 1) the fast loop has a return tie-in point at a lower pressure upstream of the sampling point, returning the sample from the fast loop at a lower pressure enables an initial pressure reduction stage (from high to medium pressure) in the fast loop. In a preferred form, the fast loop also contains a sampling point, allowing samples to be taken from the fast loop for analyses in onshore laboratories.

Gas in the fast loop is taken off to be passed to the different analysers, and subjected to one or more pressure reduction stages as appropriate. Several analysers might share sampling point and pressure reduction stages if the analyser input pressures are similar. Since the pressure inside the container is at (or near to) atmospheric, and the temperature in the container is maintained at a desired level, ordinary top-side analysers can be used with little or no modification, and so it is highly likely that in practice the input pressures of the analysers will be similar.

For most of the gas quality analysers which will in practice be used in the container, the pressure of the sample needs to be reduced. At the sampling point the pressure is at export pressure, typically above 150 bar, and many analysers require samples to be at (or close to) atmospheric pressure.

Conditioning (pressure reducing) systems for analysers for topside use are well known. In topside equipment, it is necessary to reduce the pressure in stages, and at least two stages are necessary: first down to an intermediate pressure P0, and then down to analyser pressure (that is, atmospheric pressure or close to atmospheric pressure).

A standard top-side sample conditioning system includes a fast loop where the flow is taken from a process stream by an impact probe. From this fast loop, a stream is sampled to a second stage with heating, filtering and pressure reduction. Lastly, a third stage adjusts the final pressure of the flow fed to each analyser.

In some topside cases, the fast loop pressure is the same as the sampling pressure. For subsea sampling systems, the fast loop pressure may be reduced to P0 as long as liquids in the process stream do not potentially condense at that pressure. Flows which include glycol, which has a reduced solubility in gas when pressure is reduced, are at risk of condensation when pressure is reduced, and in such a case, fast loop pressure is preferred to be kept at P1. The details of the pressure reduction used on the gas before it enters the container will of course depend on the specific characteristics of the process stream and the gas.

The fast loop return pressure is ideally chosen as the lowest pressure to which the fast loop line can discharge to. If the flow is sampled from a stand-alone pipeline, then the fast loop pressure will be the same as the pipeline pressure (that is, P1=P0), as pressure reduction in the fast loop will require recompression work before the gas in the fast loop can be returned to the pipeline, and will also increase the risk of glycol condensation (which are undesirable). If the container is placed near to an export compressor or subsea processing facility, then the suction side of a subsea compressor or an upstream scrubber will operate at a lower pressure than export pipeline pressure (P1), and so these are good locations for the return of the fast loop line.

Operating the fast loop pressure at P0 (when P0 is lower than P1) has several benefits. Firstly, lag time is reduced; for the same mass flow, the gas will flow faster in the fast loop as pressure is lower. Secondly, less pressure reduction is needed before the gas can be led to the analysers for analysis. Thirdly, it is easier to integrate the container to the rest of the subsea facility. However, it is of course necessary that the hydrocarbons and glycol do not condense when pressure is reduced to P0.

The pressure can be reduced from P1 to P0 in various ways. A dedicated subsea solution operated with a spring or hydraulic fluid could be used. Alternatively, a spring operated down-pressure regulator for use at atmospheric conditions could be installed inside the container, without need for further modifications. A flow restrictor (such as an orifice plate) could be used; a valve that could be operated with a ROV is another alternative.

It should be noted that the Joule-Thomson effect will tend to cool the gas; as the gas exits the compressor at high temperature, the temperature is reduced when reducing the pressure to P0 due to the Joule-Thomson effect. As the expansion ratio is similar to the compression ratio experienced in the compressor, the final temperature T0 is expected to be equal or above the process temperature at the compressor suction side. This, together with insulation and additional heating (if necessary) at the pressure regulator, can be enough to ensure that there is no condensation when reducing the pressure from P1 to P0.

Each analyser is coupled to a P0 loop line inside the container (as can be seen in FIGS. 2 and 3). The pressure may need to be further reduced to the analyser intake pressure. For an analyser unit operating at an intake pressure of 2 bar, reducing the pressure from P0 to 2 bar can be achieved by an additional down-pressure regulator (which may be spring operated). Several stages might be needed.

The pressure regulators can be manually set up onshore under tested and controlled conditions, and then installed in the container. The container can then be installed on the seabed without further intervention. Drift or small pressure changes can be absorbed by periodic recalibrations, preferably at regular intervals. Any need for change of the set point after installation will entail the need for a strategy for the remote control of the relevant valves, and this may be done using hydraulic or electric actuators.

There are a large number of gas quality parameters which may need to be monitored, such as: combustion related properties, e.g. calorific value (CV) and Wobbe index (WI); hydrocarbon dew point (cricondenbar or cricondentherm); water dew point (moisture/gaseous water concentration); concentration of sulphur components (including hydrogen sulphide ($H_2S$), carbonyl sulphide (COS), mercaptans and total sulphur); oxygen concentration; carbon dioxide concentration; methanol concentration; glycol concentration (i.e. triethylene glycol, TEG, and ethylene glycol, MEG); and mercury (Hg) concentration.

However, it is not currently realistic to measure all of the above subsea, and the gas quality parameters to be monitored by the container will finally be chosen based on the metering strategy for the field. The most relevant parameters for most fields are gas composition (including C1-C5, C6+, $N_2$ and $CO_2$), which can be determined by a gas chromatograph, and water dew point; for some fields, monitoring of $H_2S$ content may also be needed. Accordingly, the container is constructed to allow for analysers for three different parameters.

Since the container is intended to be permanently located in a subsea location and thus relatively inaccessible, some redundancy may be built in to the system to reduce the risk of failure. For example, there may be two identical analysers for a single parameter, or the analysers may be capable of determining more than one parameter, Redundancy may also be required for sample probes, valves, filters and the like.

It is desirable to select one analyser for each gas quality parameter, to try to standardize the content of the container. Important selection criteria for the analyser are the required levels of maintenance and calibration, and the quality and reliability of the measurements over time. It is also advantageous if the analysers can operate at high pressure, preferably close to or at export pressure, but since the container can operate at atmospheric pressure, this high-pressure operation is less important.

For offshore installations, combustion related properties are commonly calculated based on gas compositions determined using online gas chromatographs. These installations commonly run a benchmark test on a daily or weekly basis, and the maintenance interval is 6 to 24 months.

There are some challenges related to the gas chromatographs commonly used today. Flame ionization detectors (FID) are used, but as this detector involves a flame this cannot be used subsea. In addition, most gas chromatographs have a relatively large consumption of carrier gas, and there is a need for atmospheric ventilation.

It is therefore desirable to use a specialized gas chromatograph with thermal conductivity detectors (TCD) and low consumption of carrier gas. The EnCal 3000 gas chromatograph from Elster is an example of this type of gas chromatograph, but similar gas chromatographs are available from other manufacturers. Preferably, the gas chromatograph can analyse hydrocarbons up to C6 (more preferably, C9) with a thermal conductivity detector, has a sample input pressure range of 2 to 4 bar (gauge), and a carrier gas consumption of approximately 8 ml/min.

It may also be possible to use nuclear magnetic resonance spectroscopy (NMR) and spectroscopic optical techniques. NMR interacts directly with the atomic nuclei and is sensitive to the species and location in the molecule, and so this technique can also be used for sulphur compounds and mercury. Further, as method sensitivity and resolution increase with increasing gas pressure, depressurization is not needed; however, if an NMR detector is used in the same container as a gas chromatograph, it may be necessary for these to be located in separate sections of the container, given that gas chromatographs operate at considerably lower pressure. (NMR detectors and gas chromatographs both determine gas composition, and so it is not necessary to have both types of instrument; however, this may be desirable from the point of view of redundancy.)

A wide range of available techniques are available for determination of the water content or water dew point of the gas. Capacitor based quartz crystal microbalance (QCM) and tuneable diode laser absorption spectroscopy (TDLAS) analysers are commonly used; the maintenance interval is 6 to 12 months for these types of analysers, and the quality of the measurements is better for the TDLAS analysers than capacitor- and QCM-based ones.

The analytical instruments in the container may need supplies of carrier gas and calibration gases. Gas chromatography requires a continuous supply of carrier gas and periodic supply of calibration gases. Other instruments may require calibration gases, but this will depend on the choice of instrument.

Gas bottles with carrier and calibration gases can be an integrated part of the container, or may be located in an ancillary unit (as shown in FIG. 1); alternatively, the gases may be supplied through an umbilical.

Keeping gas bottles as an integrated part of the container (or as a connected ancillary unit) will make the structure heavier, but it will make it possible to retrieve the container in one retrieval operation, and also reduces the risk of seawater ingress during installation. (The analytical instruments and the sample conditioning systems inside the container have effectively zero tolerance for sea water, and it is therefore important to avoid sea water in the gas supply. Sea water that enters during installation can be flushed out using carrier gas, but the carrier gas used for flushing is effectively wasted, and it is better to avoid ingress as much as possible.)

Supply of gases through an umbilical allows for larger gas consumption, and reduces the size and weight of the container. However, there is a risk of sea water ingress through the connection to the umbilical during installation and replacement of the container. Means (such as a flushing means, filters, absorption materials or the like) may be provided to avoid damage to the analytical instruments and sample conditioning system.

Carrier gas is used in gas chromatography to transport the sample from the injector, through the column and to the detector. As discussed above, it is likely that a thermal conductivity detector (TCD) will in practice be used for subsea application. In this case, it is important that the differences in thermal conductivity between the carrier gas and the compounds to be measured are as large as possible, and high purity helium (that is, helium 5.0, 99.999%) is normally used as carrier gas for natural gas analysis with gas chromatographs.

Normally, gas chromatographs require a continuous flow of carrier gas at all times. If the carrier gas is supplied from gas bottles in the container, it may be important to choose a gas chromatograph with a low consumption of carrier gas. A micro gas chromatograph with MEMS (Micro Electro Mechanical Systems) technology uses one or two 50 litre bottles of helium per year. High purity helium is available in 50 litre bottles with filling pressure of 200 bar. For designs requiring larger carrier gas consumption, a dedicated line in an umbilical from a nearby host may be preferred. Of course, if analytical devices which do not need carrier gas are used, then the overall need for gas can be reduced, and possibly even eliminated, which is clearly advantageous in subsea applications.

Calibration gases need to be accurate, stable and homogeneous mixtures. The concentration for each component is given, together with a guaranteed accuracy of the certified value within a given time period. For gas mixtures with hydrocarbons, $CO_2$ and $H_2S$, the mixture is normally guaranteed to be stable for a period of 12 to 36 months.

Limitations in temperatures for storage and use of the calibration gases depend on the composition of the gas. The general recommendation is 20° C., but it is normally possible to store and use the gases at lower temperatures, as long as the gas mixture is kept above the condensation temperature of the mixture at all times. The condensation temperature varies with pressure and composition, and will therefore vary for each calibration gas. If the gas is stored in bottles in a gas storage cabinet (as part of the container or as an ancillary unit), then it may be necessary to heat the gas storage cabinet to avoid this problem. Calibration gases will contain hydrocarbons, and the formation of gas hydrates in the calibration gas supply system must also be avoided.

Consumption of calibration gases is relatively small compared to carrier gas, as calibration gases are only used periodically. Accordingly, it may be easiest to keep the supply of calibration gas as an integrated part of the container, rather than supplying through an umbilical.

Analysers that require low pressure samples will produce an exhaust gas, which (for gas chromatographs) will consist of carrier gas, calibration gas or sample, possibly together with remaining sample gas after sampling and pressure reduction. Analysers can in general be sensitive to back-pressure (that is, the pressure of the exhaust gas), and so if the analysers are to operate at low pressure it is necessary to deal with the exhaust gas. The exhaust gas may be vented to a large volume (as in FIG. 2) to reduce the perturbation to the back-pressure.

The gas discharge from the analysers will vary with time, depending on whether the analysers are running or in stand-by/gas saving mode between analyses. The total volume of exhaust gas from the analysers will depend on the analyser technologies chosen and the design of the system for sampling and pressure reduction.

There are two alternatives regarding how to supply a damping volume for the exhaust gas; either use the container where the analysers are placed, or use a dedicated exhaust gas reservoir.

If the space in the container which accommodates the analysers is used, then the container has the double role of providing a protected environment for the analysers, and also working as the exhaust gas damping volume. This solution is shown schematically in FIG. 3. There is only one volume, and since all exhaust gases are in contact with the analysers, the gas environment might represent a hazard for the materials used in the analysers (depending on field characteristics such as content of mercury or hydrogen sulphide). Low levels of glycols and water are also to be expected, and there is a risk of a small leakage rate of sea water through the seals and feedthroughs. Further, helium diffuses easily through polymers, which may cause problems if helium is used as the carrier gas for the gas chromatograph(s), as electronic equipment can fail in helium atmospheres. A possible solution is to use process gas or nitrogen to dilute the helium.

An alternative solution (shown in FIG. 2) is to collect the exhaust gas from the analysers and the sample conditioning system in a dedicated exhaust gas volume (or reservoir). In this case, the space where the equipment is installed will be a stagnant volume filled with gas, such as nitrogen, at atmospheric pressure. The exhaust gas will be routed to a vessel in a closed system. Alternatively, the exhaust gas can be compressed (to increase its pressure) and discharged to the undersea environment, or returned to the main gas flowline.

The main advantage of using a separate volume to collect the exhaust gas is that there is no contact between the exhaust gas and the external surfaces and electronics of the analysers. This minimises the risk of complications due to pressure fluctuations, trace components in the gas (e.g. $H_2S$, $CO_2$, Hg, $H_2O$, glycol), and the presence of helium.

As the analysers contain connection points, valves and the like, there is always a possibility for leakages from the analysers. Thus, if a dedicated exhaust gas reservoir is used, there is a risk of gas leakage causing a build-up of pressure in the atmospheric pressure region where the analysers are placed. This can be dealt with by installing a pressure relief valve, which allows the gas in the atmospheric pressure region to be discharged into the exhaust gas reservoir.

For a gas chromatograph system, variations in the back pressure can influence the separation and location of the component peaks in the chromatogram, and so lead to errors in the quantification of the components. As exhaust gas is being produced, it needs to be evacuated to avoid increase of the back pressure following a pressure control strategy.

Two possible container pressure control strategies are: continuous pressure equalization by open channel to atmosphere; and batch operation with active gas extraction.

In continuous pressure equalization, a line from the container to the atmosphere can be opened via the umbilical to a host. A pressure equalization line is a passive system. As the gas is ventilated to the container, the pressure will increase slightly with time, and this increase in pressure produces a flow through the pressure equalization line. The pressure increase that will give a constant flow rate through the pressure equalization line will vary with the line length and internal diameter.

In one specific example, a 70 km 16 mm umbilical line to land will produce a pressure increase of 4 kPa, which is below the variations expected in atmospheric conditions for equipment working topside (atmospheric pressure variations in a day can span from 970 to 1050 hPa, that is, they can vary by 8 kPa). Furthermore, for constant use of carrier gas and constant exhaust gas flow rate, this increase of 4 kPa will represent a constant offset, making it possible to perform both the calibration and the normal operation with the same back pressure, even for larger distances or smaller tubing. The increase in pressure inside the exhaust container is acceptable and enough to drive the produced gas through the umbilical. The exact pressure increase will vary depending on the particular details of the container and analysers.

It should be noted that water build-up will severely affect the operation of such a line. The umbilical line needs to be kept at a minimal water content, during installation as well as in operations phase, and it may be necessary to remove water in case of water ingress.

In active removal of excess gas by batch operations, the pressure control strategy is to run measurements in batches, and to empty the exhaust volume (that is, the volume accommodating the analysers) between the batches. During measurements, the gas fills the volume and the pressure gradually increases. After a number of measurements, the pressure in the volume has reached a set pressure, and the volume needs to be evacuated to return it to the start pressure.

Evacuation should not take place during analysis, to avoid pressure fluctuations that may affect the quality of the measurements. The number of measurements per batch will depend on the amount of gas released from the different analysers, the rate of build-up of pressure in the volume, and the analysers' tolerance for variations in the back-pressure. The duration of the batch should also be adapted to the cycle time needed for each analysis. The excess gas will be a mixture of process gas, carrier gas and calibration gas. This needs to be returned either to a low pressure process stream or discharged to sea.

Active removal of the contained volume may be achieved by a hydraulic driven gas booster, an electric driven reciprocating compressor, or an ionic liquid piston compressor.

It is possible to carry out continuous (or at least frequent) sampling and analysis, or to run batch sampling and/or analysis. In one version, samples are taken less frequently from the fast loop for depressurisation and analysis. In a second version, samples are taken periodically and are collected in a container to be analysed (for example, around once per day).

During continuous (or frequent) operation, the consumption of carrier gas by the gas chromatograph is uninterrupted, regardless of whether a sample is being analysed or not. However, in batch operation, the flow of carrier gas is interrupted while the gas chromatograph is not active. This may therefore reduce the wear on the analysers (which can be an important consideration given that the container must be retrieved to the surface if the analysers are to be repaired or replaced), reduce the carrier gas consumption, and reduce the amount of exhaust gas produced.

However, gas chromatographs are normally designed to run with a continuous flow of carrier gas through the system, as heating of the column without carrier gas flow can result in severe damage to the column. The question of whether to use continuous analysis or batch analysis will vary depending on the details of the installation. It may also be possible to reduce the pressure of the carrier gas, and hence the gas flow through the gas chromatograph, between analyses.

Additional heating and insulation to that already mentioned may be needed in parts of the system; for example, to heat lines to avoid condensation, to compensate for Joule-Thomson effects during pressure reduction, and to compensate for heat loss to the surrounding sea water (although this can be minimized by using insulation). In addition, heating may be required to maintain the quality of the calibration gases.

Heating may be needed in the fast loop, although a lower pressure in the fast loop will allow less mass flow for the same residence time requirement, which reduces the heating needs. A higher temperature might be needed to avoid glycol condensation. As the analysers use small gas volumes, heating power requirements downstream of the fast loop will be very low.

The maintenance philosophy for the analysis system is to exchange the gas quality analysis container with a spare fully equipped container when maintenance needs arise, or at a given interval if no such needs have arisen in that interval. The interval depends on the weakest link in the system, but the goal is for a maintenance interval of two years or more. The equipment will in practice be chosen (and, if necessary, improved) with respect to its maintenance and calibration needs.

Maintenance will be performed at an onshore workshop, and a replacement container needs to be available at the onshore base at all times in case of sudden failure.

It would be desirable to install two redundant analysers for each parameter. This would make the system more robust, and will be beneficial in cases where an analyser fails or encounters problems between planned maintenance operations. Redundant analysers will reduce the uncertainty in the measurements, and this also allows an operator to detect errors or uncertainties in the measurements by comparing the two measurements from the analysers. However, a system with redundant analysers will be more complex and expensive. Larger volumes of carrier and calibration gases will be required, more exhaust gas will be produced, and the size and weight of the container will be increased.

Periodic quality control and calibration of the analysers is important to maintain the quality of the measurements. The container will have a supply of carrier gases based on demand, but systems for automatic calibration may need to be adapted or developed. The need for manual calibration should be in agreement with the planned replacement interval for the container, and should therefore be kept at a minimum.

The installation and connection method will follow the installation principle for the field; installation on guide wire system is assumed, but this will depend on the installation method applied for the specific field. It is here assumed that there will be one large module and possibly several smaller modules which are separately retrievable. There will be a number of hydraulic and electrical jumpers to connect as well.

Replaceable units are typically in the range of 2,000 to 10,000 kg, and the unit should be kept in that range to allow for simple installation and retrieval. However, heavier units (with weight up to 60 tons) can be handled by IMR (inspection, maintenance and repair) vessels.

Separate installation and retrieval may be considered for control electronics, accumulators and other components.

Connection and operation should be done by ROV. Divers may be an alternative at shallow water depth.

Suitable connectors for process connections may be hydraulic couplers. These couplers have poppets restricting the amount of water entering during mating and demating operations. A few millilitres of water penetration are minimum water influx during hook up. This needs to be flushed out to the flowline via the fast loop as even the smallest traces of water may damage the analysers.

The system requires calibration gas and carrier gas to be stored in bottles or pressure accumulators. The lines for these gases have zero tolerance for water ingress. In order to avoid subsea couplers on the gas lines the accumulators should be part of the main module and not an independently retrievable module.

The equipment is expected to be installed in conjunction with a subsea processing facility. The equipment will be powered electrically. Communication interface should be Ethernet according to SIIS (subsea instrument interface standardization) level 3, as this enables straightforward integration to control systems. Fibre communication is preferred, as this provides sufficient communication speed.

If power consumption is less than 96 watts, the equipment can be powered direct from the SIIS 3 interface and will not require any extra power connection. However, it is expected that power consumption will be greater than this in practice, and so an alternative power supply will in most cases be required.

Dedicated electronics can be placed in a separate sealed atmospheric pressure chamber. Inside the chamber there will be nitrogen at atmospheric pressure. The sealed chamber should reside in an oil filled pressure compensated chamber. All external connections (fibre, electrical) are through glass-metal penetrators.

The present invention has been made in the context of a process stream of natural gas, but may have wider applicability.

The invention claimed is:

1. Apparatus for monitoring the quality of gas in a process stream at a subsea location comprising:
    a container for installation at the location;
    one or more devices for analysing gas quality, said devices being located in the container, wherein at least one of the devices for analysing gas quality is a gas chromatograph; and
    a line for supplying a sample of gas from the process stream to the said one or more devices;
    wherein the pressure within the container is maintained at or near to atmospheric pressure,
    the apparatus further comprising a reservoir for supplying carrier gas and/or calibration gas to the gas chromatograph, the reservoir holding said carrier gas and/or calibration gas, and said reservoir being in the form of one or more gas bottles.

2. Apparatus as claimed in claim 1, further comprising a pressure regulator for reducing the pressure of the sample of gas from the pressure of the process stream to the pressure within the container.

3. Apparatus as claimed in claim 1, further comprising means for discharging gas from the container after analysis.

4. Apparatus as claimed in claim 3, wherein said means for discharging gas includes a reservoir for the analyzed gas.

5. Apparatus as claimed in claim 4, further comprising an umbilical for removing gas from said reservoir.

6. Apparatus as claimed in claim 1, further comprising a heating device for controlling the temperature within said container.

7. A method of monitoring the quality of gas in a process stream at a subsea location, including the steps of:
    installing a container at said subsea location, said container including a volume at or near atmospheric pressure accommodating one or more devices for analysing gas quality;
    taking a sample of gas from the process stream;
    supplying said sample of gas to said one or more devices for analysis, wherein at least one of the devices for analysing gas quality is a gas chromatograph; and
    supplying carrier gas and/or calibration gas to the gas chromatograph, wherein the carrier gas and/or the calibration gas is supplied by a reservoir holding said carrier gas and/or calibration gas, said reservoir being in the form of one or more gas bottles.

8. A method as claimed in claim 7, further comprising the step of reducing the pressure of the sample of gas to or to near to atmospheric pressure before supplying said sample to said one or more devices.

9. A method as claimed in claim 7, further comprising the step of discharging gas after analysis.

10. A method as claimed in claim 7, wherein said sample taken from the process stream is in a single phase.

11. A method as claimed in claim 7, wherein said sample taken from the process stream includes a gas phase and a liquid phase, which are analysed separately.

12. A method as claimed in claim 7, further comprising the step of controlling the temperature within the container.

13. Apparatus for monitoring the quality of gas in a process stream at a subsea location comprising:
    a container for installation at the location;
    one or more devices for analysing gas quality, said devices being located in the container, wherein at least one of the devices for analysing gas quality is a gas chromatograph; and
    a line for supplying a sample of gas from the process stream to the said one or more devices;
    wherein the pressure within the container is maintained at or near to atmospheric pressure,
    the apparatus further comprising an umbilical for supplying carrier gas and/or calibration gas to the gas chromatograph.

14. Apparatus as claimed in claim 13, further comprising a pressure regulator for reducing the pressure of the sample of gas from the pressure of the process stream to the pressure within the container.

15. Apparatus as claimed in claim 13, further comprising means for discharging gas from the container after analysis.

16. Apparatus as claimed in claim 15, wherein said means for discharging gas includes a reservoir for the analyzed gas.

17. Apparatus as claimed in claim 16, further comprising an umbilical for removing gas from said reservoir.

18. Apparatus as claimed in claim 13, further comprising a heating device for controlling the temperature within said container.

19. A method of monitoring the quality of gas in a process stream at a subsea location, including the steps of:
- installing a container at said subsea location, said container including a volume at or near atmospheric pressure accommodating one or more devices for analysing gas quality;
- taking a sample of gas from the process stream;
- supplying said sample of gas to said one or more devices for analysis, wherein at least one of the devices for analysing gas quality is a gas chromatograph; and
- supplying carrier gas and/or calibration gas to the gas chromatograph, wherein the carrier gas and/or the calibration gas is supplied by an umbilical.

* * * * *